US00PP35602P2

(12) United States Plant Patent
Meilland

(10) Patent No.: US PP35,602 P2
(45) Date of Patent: Jan. 30, 2024

(54) HYBRID TEA ROSE PLANT NAMED 'MEICTARUS'

(50) Latin Name: *Rosa hybrida*
Varietal Denomination: MEICTARUS

(71) Applicant: The Conard Pyle Company, West Grove, PA (US)

(72) Inventor: Alain Antoine Meilland, Antibes (FR)

(73) Assignee: THE CONARD PYLE COMPANY, West Grove, PA (US)

( * ) Notice: Subject to any disclaimer, the term of this patent is extended or adjusted under 35 U.S.C. 154(b) by 0 days.

(21) Appl. No.: 18/134,738

(22) Filed: Apr. 14, 2023

(51) Int. Cl.
*A01H 5/02* (2018.01)
*A01H 6/74* (2018.01)

(52) U.S. Cl.
USPC ..... Plt./137

(58) Field of Classification Search
USPC ..... Plt./101, 130, 137
See application file for complete search history.

(56) References Cited

U.S. PATENT DOCUMENTS

PP28,659 P3 11/2017 Meilland
PP33,493 P2 * 9/2021 Meilland ..... A01H 6/749 Plt./133

* cited by examiner

*Primary Examiner* — Karen M Redden
(74) *Attorney, Agent, or Firm* — Panitch Schwarze Belisario & Nadel LLP; Stephany G. Small; Travis W. Bliss

(57) ABSTRACT

A new and distinct variety of rose plant, referred to by its cultivar name, 'MEICTARUS', is disclosed. The new variety forms attractive, very double pink-colored flowers. Attractive semi-glossy foliage is formed, which contrasts beautifully with the blossoms. A shrub growth habit is displayed. The new variety is well suited for providing attractive ornamentation in the landscape.

1 Drawing Sheet

Latin name of genus and species of plant claimed: *Rosa hybrida.*

Variety denomination: 'MEICTARUS'.

STATEMENT REGARDING PRIOR DISCLOSURES BY THE INVENTOR

The first offer for sale of the new variety was Jul. 14, 2022, in the U.S. The first offer for sale of the new variety was by the inventor or another who obtained the new variety directly or indirectly from the inventor. No plants of the new variety have been sold in this country or anywhere in the world, nor has any disclosure of the new plant been made, more than one year prior the effective filing date of this application, and such sale or disclosure within one year was either derived directly or indirectly from the inventor.

BACKGROUND OF THE INVENTION

The new variety of hybrid tea rose plant of the present invention was created by controlled breeding at Le Cannet des Maures, Var, France by artificial pollination wherein two parents were crossed which previously had been studied in the hope that they would contribute the desired characteristics. The female parent (i.e., the seed parent) of the new variety was the 'TAN99176' variety (not patented). The male parent (i.e., the pollen parent) of the new variety was the 'ADAHUIN' variety (not patented).

The parentage of the new variety can be summarized as follows:

'TAN99176' x 'ADAHUIN'

The seeds resulting from the above pollination were sown and small plants were obtained which were physically and biologically different from each other. Selective study resulted in the identification of a single plant of the new variety.

The new variety has been found to undergo asexual propagation in Le Cannet des Maures, Var, France by a number of routes, including eye budding, softwood cuttings, semi-hardwood cuttings, and hardwood cuttings. Asexual propagation by the above-mentioned techniques in Le Cannet des Maures, Var, France has shown that the characteristics of the new variety are stable and are strictly transmissible by asexual propagation from one generation to another. Accordingly, the new variety undergoes asexual propagation in a true-to-type manner.

SUMMARY OF THE INVENTION

It was found that the new variety of rose plant of the present invention possesses the following combination of characteristics:

(a) forms a romantic pink colored flower,
(b) produces very double flowers, and
(c) exhibits a shrub growth habit.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the 'TAN99176' variety (i.e., the seed parent) exhibits a climbing growth habit, whereas the new variety exhibits a shrub growth habit. In addition, the 'ADAHUIN' variety (i.e., the pollen parent) displays red colored flowers, whereas the new variety displays pink colored flowers. Moreover, the new variety can be readily distinguished from other similar non-parental varieties. For example, the 'Meinostair' variety (U.S. Plant Pat. No. 28,659) produces flowers that are apricot pink in color, whereas the new variety produces flowers that are pink in color and the new variety has more petals than flowers produced by the 'Meinostair' variety.

The new variety has been named 'MEICTARUS'.

BRIEF DESCRIPTION OF THE PHOTOGRAPH

The accompanying photograph of the drawing shows as nearly true as it is reasonably possible to make the same, in a color illustration of this character, typical specimens of the plant parts of the new variety. The rose plants of the new variety were approximately one year of age and were observed during September while budded by cuttings and growing outdoors at Le Cannet des Maures, Var, France. Dimensions in centimeters are indicated at the bottom of the drawing.

Element 1—illustrates a specimen of a young shoot.

Element 2—illustrates a specimen of a floral bud before the opening of the sepals.

Element 3—illustrates a specimen of a floral bud at the opening of the sepals.

Element 4—illustrates a specimen of a floral bud at the opening of the petals.

Element 5—illustrates a specimen of a flower in the course of opening.

Element 6—illustrates a specimen of an open flower—plan view—obverse.

Element 7—illustrates a specimen of an open flower—plan view—reverse.

Element 8—illustrates a specimen of a fully open flower—plan view—obverse.

Element 9—illustrates a specimen of a fully open flower—plan view—reverse.

Element 10—illustrates a specimen of a flowering stem.

Element 11—illustrates a specimen of a floral receptacle showing arrangement of the stamens and pistils.

Element 12—illustrates a specimen of a floral receptacle showing arrangement of the pistils (stamens removed).

Element 13—illustrates a specimen of a leaf with 3 leaflets—plan view—upper surface.

Element 14—illustrates a specimen of a leaf with 3 leaflets—plan view—under surface.

Element 15—illustrates a specimen of a leaf with 5 leaflets—plan view—upper surface.

Element 16—illustrates a specimen of a leaf with 5 leaflets—plan view—under surface.

Element 17—illustrates a specimen of a leaf with 7 leaflets—plan view—upper surface.

Element 18—illustrates a specimen of a leaf with 7 leaflets—plan view—under surface.

DETAILED BOTANICAL DESCRIPTION

The chart used in the identification of the colors is that of The Royal Horticultural Society (The R.H.S. Colour Chart, 2001 edition), London, England. The terminology which precedes reference to the chart has been added to indicate the corresponding color in more common terms. The description is based on the observation of one-year-old specimens of the new variety during September while budded by cuttings and growing outdoors at Le Cannet des Maures, Var, France.

Botanical classification: *Rosa hybrida* cultivar MEICTARUS.

Commercial classification: Hybrid Tea Rose Plant.

Plant:

*Habit*.—Shrub.

*Height*.—Approximately 100 cm on average.

*Width*.—Approximately 100 cm on average.

Branches:

*Color*.—Young stems: commonly near Green Group 143C suffused with near Greyed-Orange Group 177B. Adult wood: commonly near Yellow-Green Group 147C.

*Length*.—From the crown to the flower is typically between 40 cm to 70 cm.

*Diameter*.—Typically between 0.6 cm to 1.0 cm on average.

*Young shoots*.—Anthocyanin coloration: commonly near Greyed-Orange Group 177B.

*Thorns*.—Configuration on adult stems: slightly concave and elongated on the upper surface; and curved downwards on the under surface. Long prickles — quantity: commonly 2 thorns per 10 cm long young stem and commonly 6 thorns per 10 cm long adult stem. Long prickles — length: typically between 0.4 cm to 0.5 cm on young stems and approximately 0.4 cm on adult stems. Long prickles — base shape: narrow oval on young stems and narrow obovate on adult stems. Long prickles — color on young stems: commonly near Yellow-Green Group 146B suffused with near Greyed-Orange Group 176B. Long prickles — color on adult stems: commonly near Greyed-Orange Group 165A at the base to near Greyed-Orange Group 166A at the top. Small prickles — quantity: absent on young stems; commonly 7 thorns per 10 cm long adult stem. Small prickles — length: approximately 0.1 cm on average. Small prickles — base shape: broad oval. Small prickles — color: commonly near Greyed-Orange Group 165A.

*Internode*.—Numbers on the entire branch: typically between 12 to 22. Length: typically between 2.0 cm and 3.5 cm.

Foliage:

*General appearance*.—Very dense, with a semi-glossy aspect.

*Number of leaflets*.—3, 5, 7; most often 5.

7 *leaflets leaf*.—Length: typically between 11.0 cm to 12.0 cm. Width: typically between 8.0 cm to 9.5 cm.

*Terminal leaflet*.—Length: typically between 5.0 cm to 5.5 cm. Width: typically between 3.2 cm to 3.5 cm.

*New foliage*.—Upper surface color: commonly near Yellow-Green Group 147A suffused with near Greyed-Purple Group 187B. Under surface color: commonly near Yellow-Green Group 147B suffused with near Greyed-Purple Group 187B.

*Adult foliage*.—Upper surface color: commonly near Green Group 137A. Under surface color: commonly near Green Group 138B. Anthocyanin coloration: very slight, commonly near Greyed-Orange Group 177B on under surface.

Leaflets:

*Shape*.—Top: acuminate. Base: obtuse to rounded.

*Intensity of glossiness*.—Medium.

*Texture*.—Upper surface is leathery, smooth; under surface is bumpy.

*General appearance*.—Oval.

*Serration*.—Small and single.

*Undulation on the margin*.—Medium.

*Venation*.—Color is commonly near Yellow-Green Group 144A on the upper surface and near Yellow-Green Group 144B on the under surface; pattern is imparipinnate.

*Petiole rachis*.—Color of upper surface: commonly near Yellow-Green Group 144A. Color of under surface: commonly near Yellow-Green Group 144B. Texture: upper surface is few glandular, under surface is few prickles. Rachis of terminal leaflet: length is approximately 3.5 cm and diameter is typically 0.15 cm to 2.0 cm.

*Petioles*.—Upper surface: few glandular. Under surface: no prickles. Color of upper surface: commonly near Yellow-Green Group 144A. Color of under surface: commonly near Yellow-Green Group 144B. Length: typically between 2.5 cm to 3.5 cm. Diameter: typically between 0.15 cm to 0.2 cm.

*Stipules*.—Length: typically between 1.5 cm to 1.7 cm. Width: typically between 0.15 cm to 0.2 cm. General appearance: narrow. Texture: smooth. Color of upper surface: commonly near Yellow-Green Group 144B. Color of under surface: commonly near Yellow-Green Group 144C.

Inflorescence:

*Number of flowers per stem*.—Between 1 to 5 flowers per stem.

*Lastingness of the bloom*.—On the plant: approximately 7 days on average. In vase: not tested.

*Bud*.—Shape: conical. Size: medium. Length: approximately 3.0 cm on average. Width: approximately 2.5 cm on average. Color as calyx breaks: upper surface: commonly near Red-Purple Group 62D, basal spot is very little and near Greyed-Yellow Group 160C. under surface: commonly near Red-Purple Group 62D suffused with near Red-Purple Group 57B, basal spot is very little and near Greyed-Yellow Group 160C.

*Sepals*.—Number: commonly 5. Length: typically between 1.5 cm to 3.0 cm. Width: typically between 0.5 cm to 0.8 cm on median part. Shape: elongated and narrow. Extensions: present, very weak typically between 0.2 cm to 0.6 cm in length. Upper surface: texture: tomentous. color: commonly near Green-White Group 157A. Under surface: texture: smooth. color: commonly near Yellow-Green Group 144A slightly suffused with near Greyed-Orange Group 176A.

*Receptacle*.—Color: commonly near Yellow-Green Group 144B. Length: approximately 0.6 cm on average. Width: approximately 0.6 cm on average. Surface: smooth. Shape: funnel shaped.

*Peduncle*.—Length: typically between 2.0 cm to 2.5 cm. Width: approximately 0.3 cm on average. Surface: glandular. Color: commonly near Yellow-Green Group 144A slightly suffused with near Greyed-Orange Group 176A.

*Flower*.—Diameter when open: approximately 8.0 cm. Shape: cup shaped. Shape when viewed from above: irregular rounded. Type: very double. Number of petals under normal conditions: approximately 70 on average. Petals: shape: attenuated at the base and rounded at the top; general shape is conical. texture: medium hard. length: typically between 2.0 cm to 4.0 cm. width: typically between 1.8 cm to 4.5 cm. Undulation of the petal: weak. Reflexing of the petal: absent. Petal incision: medium. Petal arrangement: imbricated without petaloids. Petal drop: petals drop off cleanly before drying. Fragrance: strong (lychees and slight grapefruit). Discoloration of the flower: no. Color when opening: basal spot on the upper surface: commonly near Greyed-Yellow Group 160C. upper surface: commonly near Red-Purple Group 62D. basal spot on the under surface: commonly near Greyed-Yellow Group 160C. under surface: commonly near Red-Purple Group 62D suffused with near Red-Purple Group 57B. Color of the open flower: basal spot on the upper surface: commonly near Greyed-Yellow Group 160A. upper surface of the flower: commonly near Red Group 36D edged with near Red-Purple Group 62B. basal spot on the under surface: commonly near Greyed-Yellow Group 160B. under surface of the flower: commonly near Red-Purple Group 62D suffused with near Red-Purple Group 57C. Anthers: number is typically between 15 to 20, length is approximately 0.2 cm on average, width is approximately 0.1 cm on average, coloration is commonly near Greyed-Orange Group 163A, and arrangement is regular around styles. Filaments: length is typically between 0.3 cm and 0.9 cm and coloration is commonly near Greyed-Yellow Group 160A at the base to Greyed-Orange Group 172C at the top. Styles: length is typically between 0.4 cm to 0.8 cm, coloration is commonly Greyed-Purple Group 185C, and number is approximately 60 on average. Stigmas: length is commonly less than 0.1 cm and coloration is commonly near Greyed-Yellow Group 161A. Pollen: not available. Hips: very rare, no additional information available.

Development:

*Vegetation*.—Strong.

*Blooming*.—Early in the season, abundant and recurrent from May to the first frosts in France.

*USDA hardiness zone*.—Zone 5 to 10.

*Tolerance to disease*.—Good, and particularly against rust (*Phragmidium* sp.) and mildew (*Peronospora sparsa*).

The new 'MEICTARUS' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of rose plant named 'MEICTARUS' characterized by the following combination of characteristics:

(a) forms a romantic pink colored flower, (b) produces very double flowers, and (c) exhibits a shrub growth habit;

substantially as herein shown and described.

* * * * *

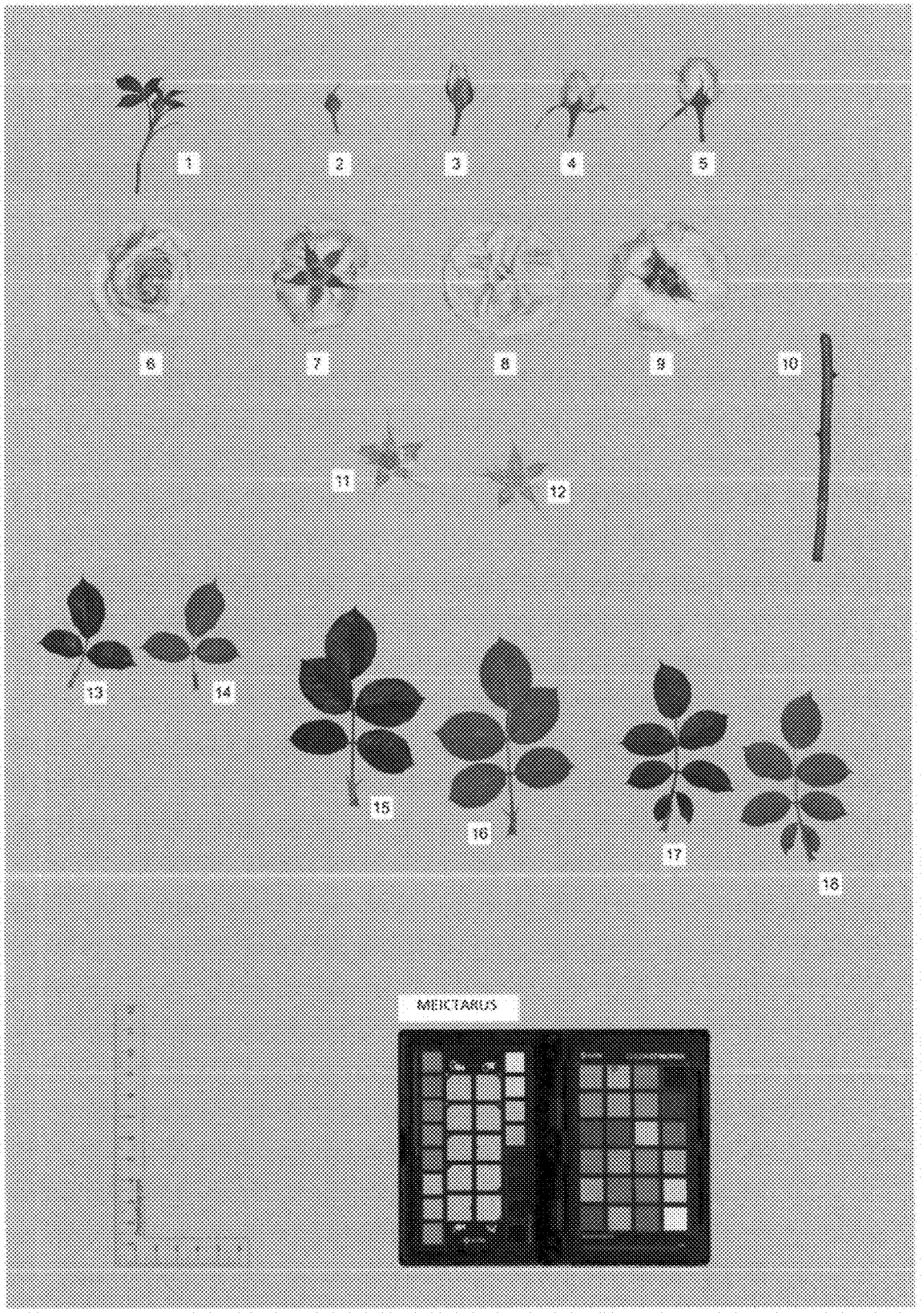
1
2
3
4
5
6
7
8
9
10
11
12
13
14
15
16
17
18
NECTARUS